(12) United States Patent
Keenan

(10) Patent No.: US 9,227,027 B2
(45) Date of Patent: Jan. 5, 2016

(54) THREE-POINT CHILD RESISTANT LID

(71) Applicant: MeadWestvaco Corporation, Richmond, VA (US)

(72) Inventor: Joseph Francis Keenan, Superior, CO (US)

(73) Assignee: WestRock MWV, LLC, Norcross, GA (US)

( * ) Notice: Subject to any disclaimer, the term of this patent is extended or adjusted under 35 U.S.C. 154(b) by 72 days.

(21) Appl. No.: 14/211,195

(22) Filed: Mar. 14, 2014

(65) Prior Publication Data

US 2014/0263455 A1    Sep. 18, 2014

Related U.S. Application Data

(60) Provisional application No. 61/787,448, filed on Mar. 15, 2013.

(51) Int. Cl.
| | | |
|---|---|---|
| *B67B 3/00* | (2006.01) | |
| *A61M 15/00* | (2006.01) | |
| *A61M 15/08* | (2006.01) | |
| *A61M 11/00* | (2006.01) | |
| *B05B 11/00* | (2006.01) | |

(52) U.S. Cl.
CPC ......... *A61M 15/0026* (2014.02); *A61M 11/006* (2014.02); *A61M 15/08* (2013.01); *B05B 11/0032* (2013.01); *B05B 11/3059* (2013.01); *A61M 15/009* (2013.01); *A61M 2205/276* (2013.01); *B05B 11/001* (2013.01)

(58) Field of Classification Search
CPC .......... A61M 15/0026; A61M 15/009; A61M 2205/276; A61M 11/006; A61M 15/08; B05B 11/0032; B05B 11/3059; B05B 11/001
USPC .................................. 222/153.13, 182, 321.6
See application file for complete search history.

(56) References Cited

U.S. PATENT DOCUMENTS

| | | | | |
|---|---|---|---|---|
| 5,207,657 A | * | 5/1993 | Gibilisco ............. | A61M 35/003 201/216 |
| 6,173,868 B1 | * | 1/2001 | DeJonge ........... | A61M 15/0065 222/153.13 |
| 7,757,901 B2 | * | 7/2010 | Welp ................... | B05B 11/0032 222/153.13 |
| 2003/0106901 A1 | * | 6/2003 | Meshberg ........... | B05B 11/0013 222/1 |

* cited by examiner

*Primary Examiner* — Kevin P Shaver
*Assistant Examiner* — Robert Nichols, II
(74) *Attorney, Agent, or Firm* — WestRock Intellectual Property Group

(57) ABSTRACT

A safety device for a nasal spray applicator may include a two or three-point safety engagement feature to retain a protective cap or cover over the nasal spray applicator and to prevent or restrict actuation thereof.

7 Claims, 6 Drawing Sheets

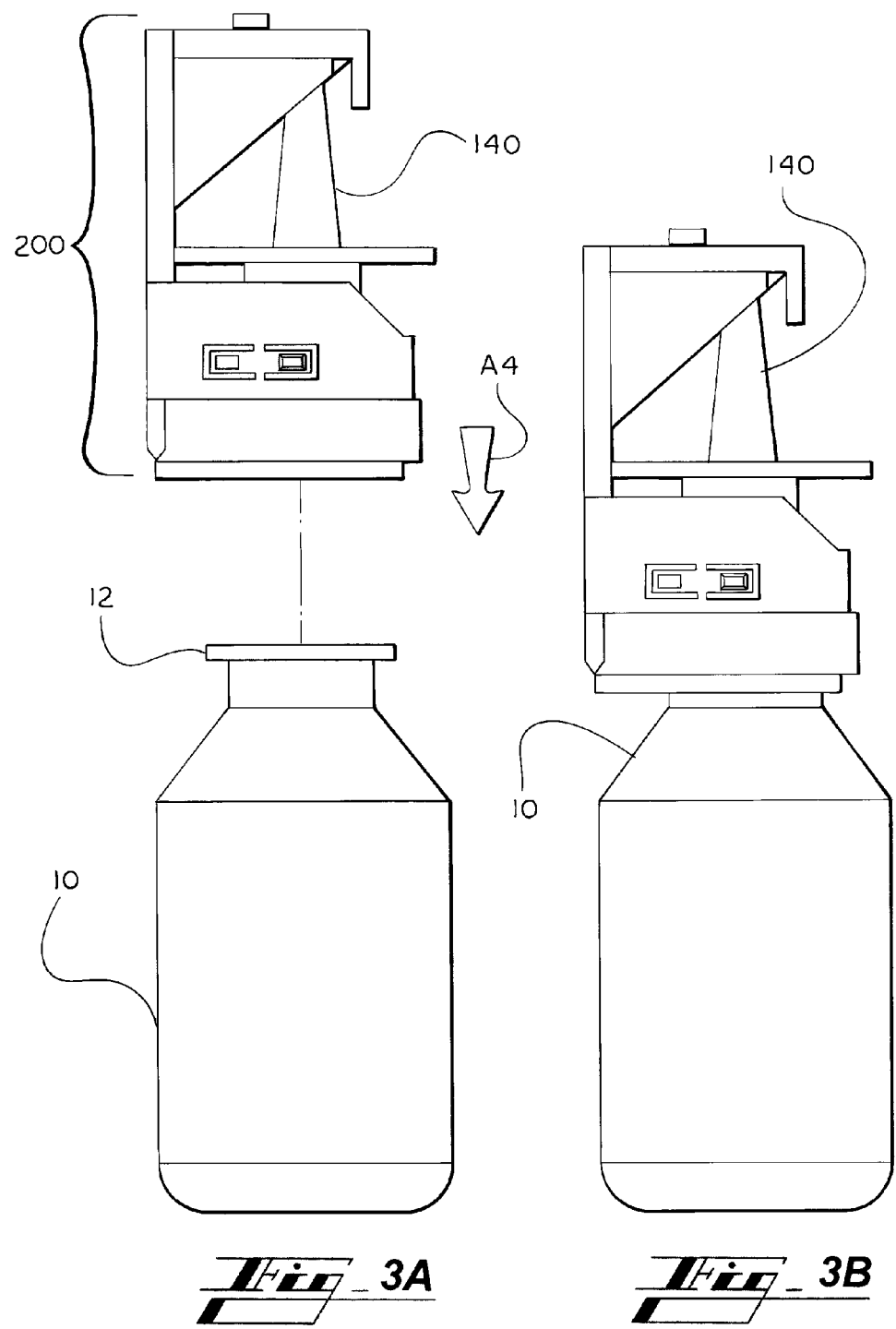

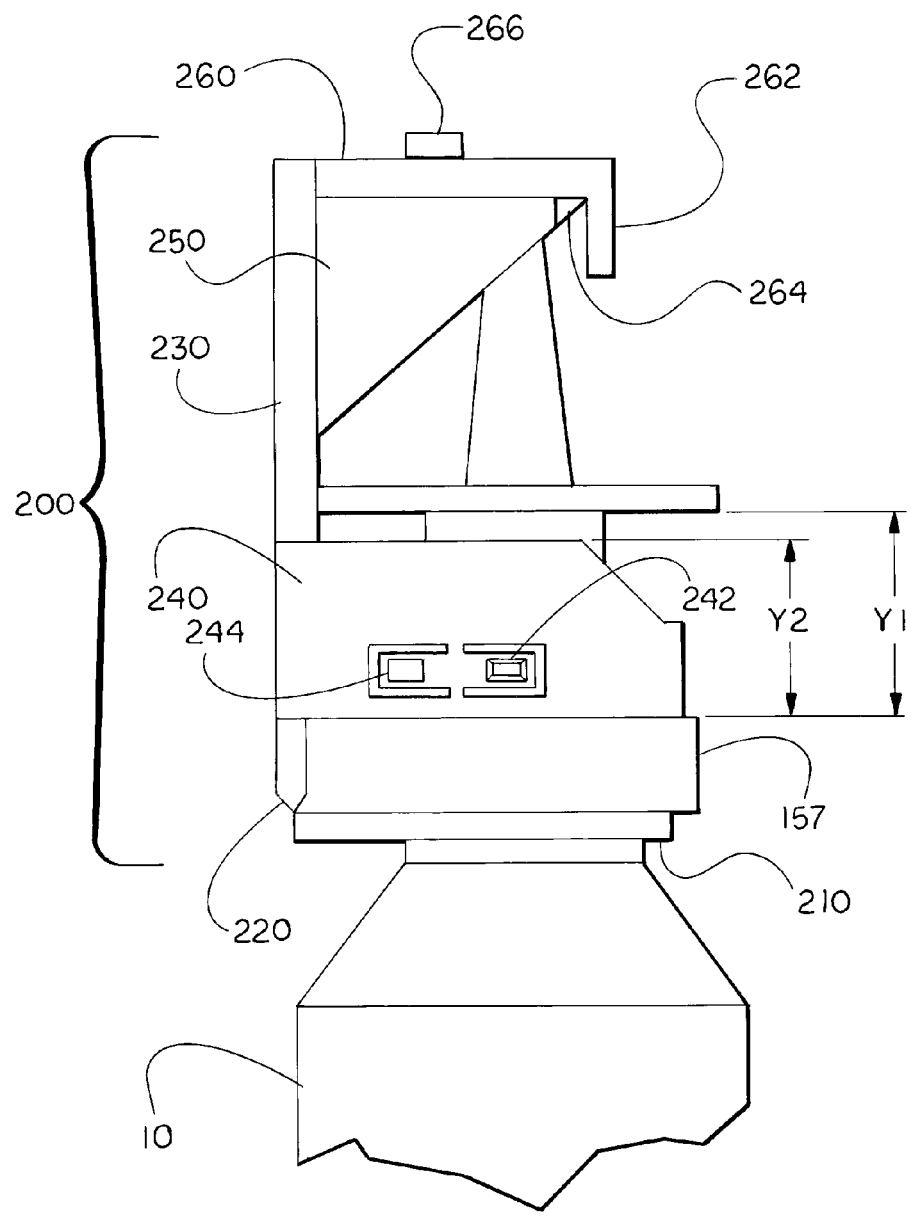
Fig_4

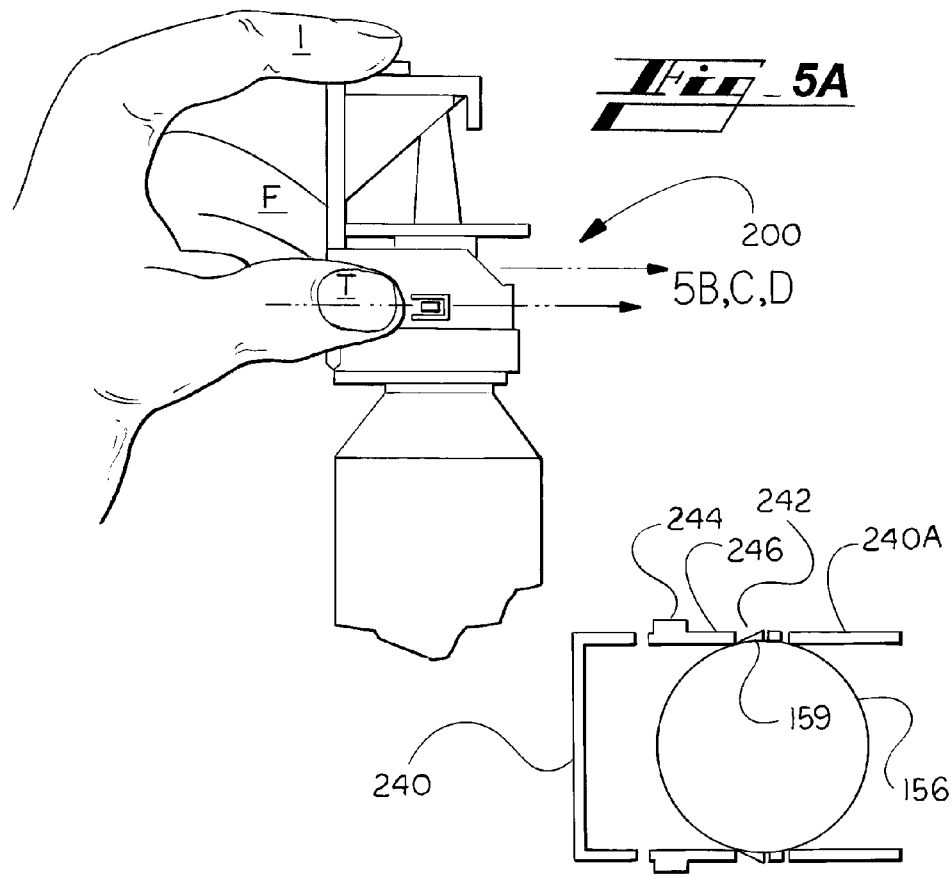
Fig_5A
Fig_5B
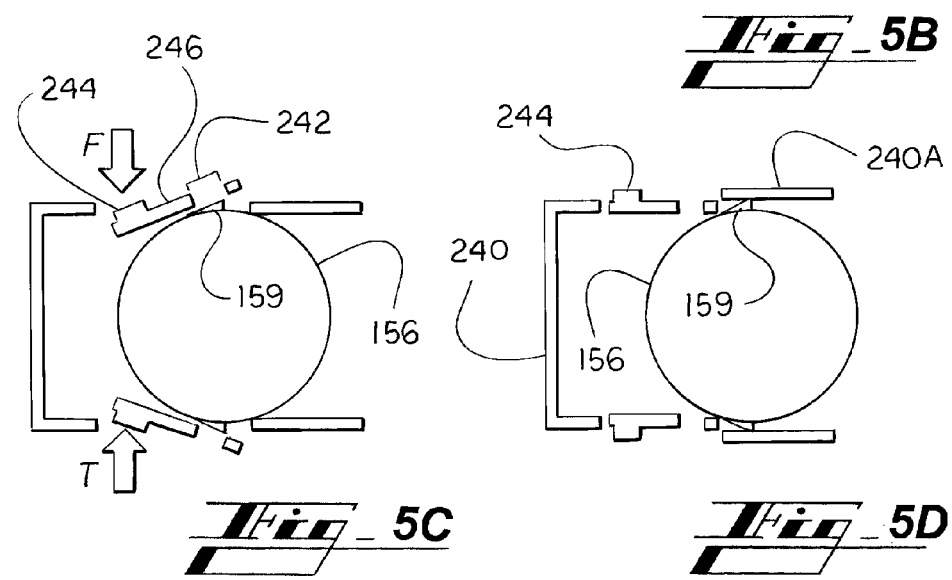
Fig_5C
Fig_5D

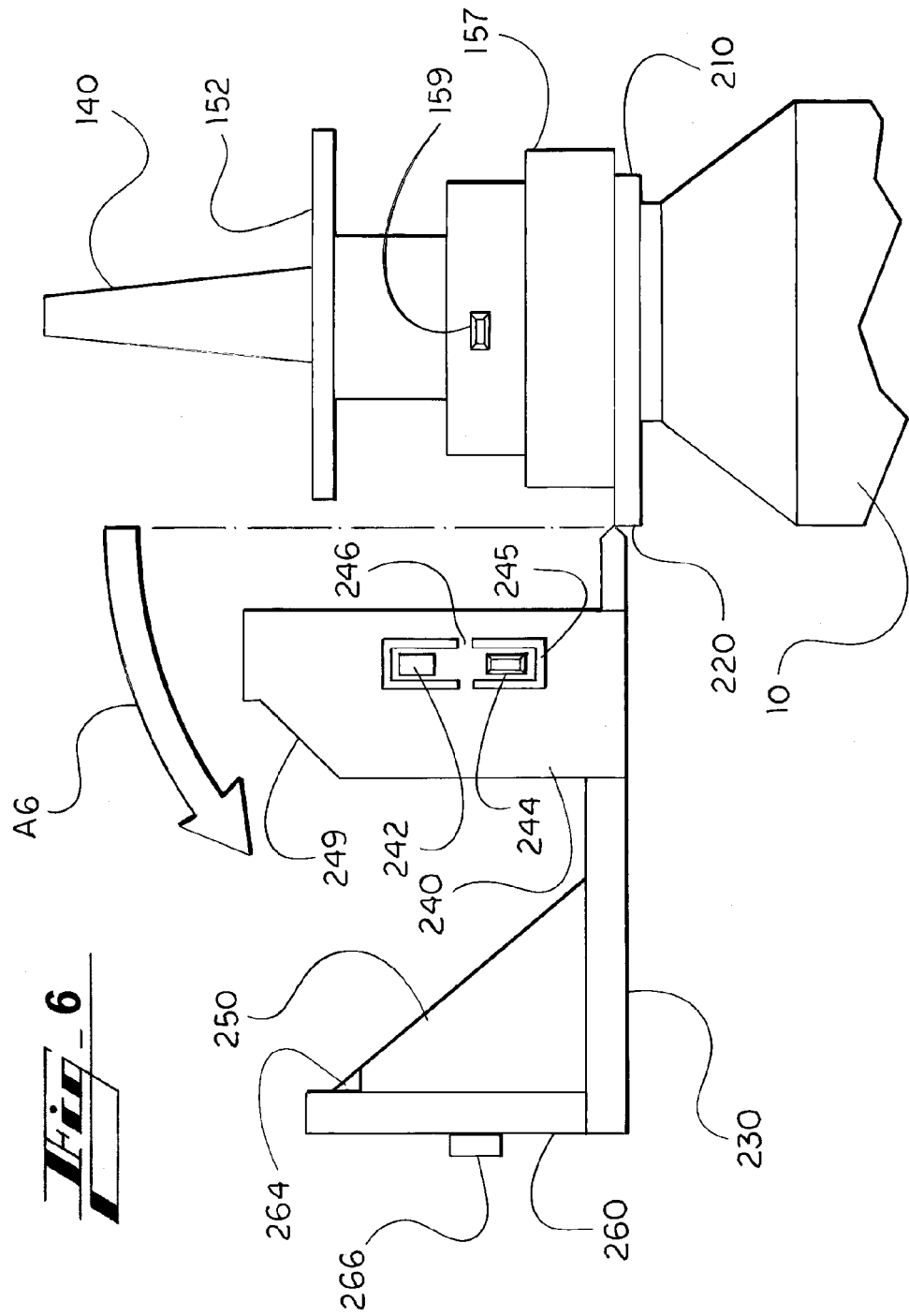

THREE-POINT CHILD RESISTANT LID

CROSS-REFERENCE TO RELATED APPLICATIONS

This application claims the benefit of U.S. Provisional Application No. 61/787,448, filed Mar. 15, 2013, and incorporates the same herein by reference in its entirety.

BACKGROUND OF THE INVENTION

1. Field of the Invention

Closure lids for dispensing containers, particularly child resistant lids and more particularly, closure lids with three-point locking features.

2. State of the Art

Dispensing containers are commonly used for dispensing contents in the form of liquids, pastes, or powders which may include medications, adhesives, and the like. It is often desired to limit access to the contents of such containers, so that children are not able to easily dispense the contents. Various child-resistant devices may be incorporated into dispensing containers. An improved child resistant closure is desired.

BRIEF SUMMARY OF THE INVENTION

In one embodiment, a safety device is disclosed that may be applied to a dispenser of the type actuated by an axial compression of a dispenser nozzle. The safety device may include a base portion secured to the dispenser nozzle or to a container attached to the dispenser nozzle; an axial portion with a first end hingedly attached to the base portion; and a terminal portion attached to the axial portion at a second end opposite from the first end. The terminal portion may have a tooth for engaging an outlet end of the dispenser nozzle; a pair of side portions attached to the axial portion between the first and second ends, and the side portions may each have a side engagement feature for engaging a side of the dispenser nozzle. The safety device may have a safety position and a dispense position, such that the tooth and the two side engagement features each must be disengaged before the safety device can be moved from the safety position to the dispense position.

BRIEF DESCRIPTION OF THE DRAWINGS

While the specification concludes with claims particularly pointing out and distinctly claiming particular embodiments of the present invention, various embodiments of the invention can be more readily understood and appreciated by one of ordinary skill in the art from the following descriptions of various embodiments of the invention when read in conjunction with the accompanying drawings in which:

FIGS. 3A-3B illustrate of the nasal spray applicator of FIG. 2, provided with a safety device;

FIG. 4 illustrates a side detail view of the safety device in a closed configuration;

FIG. 5A illustrates a side detail view of the safety device being held by a user;

FIGS. 5B-5D illustrate cross section views as seen from the top of the safety devices, showing details of the side latches; and FIG. 6 illustrates a side detail view of the safety device in an open configuration.

DETAILED DESCRIPTION OF THE INVENTION

According to embodiments of the invention, a child resistant closure device is provided to be integrated onto an existing cap. In certain embodiments the closure may be adapted for use with a nasal pump dispenser. The closure device may provide child resistance to the contents of the nasal pump. The closure device may provide a tamper evidence feature. The closure device may provide a shipping lock feature. The closure device may remove the need for the shrink wrap sleeve. The closure may be securely connected to the usual cap of the nasal pump dispenser in order to promote the user's compliance with the child resistant feature, and to reduce loss of the closure device.

In certain embodiments the closure device may be connected to an existing cap via a living hinge. In certain embodiments the child-resistant features may include three points at which force must be applied to unlock the closure device so that the nasal pump may be actuated. The closure device may eliminate the prior need for shrink wrapping to provide a shipping lock and tamper resistance.

Figure 1A:
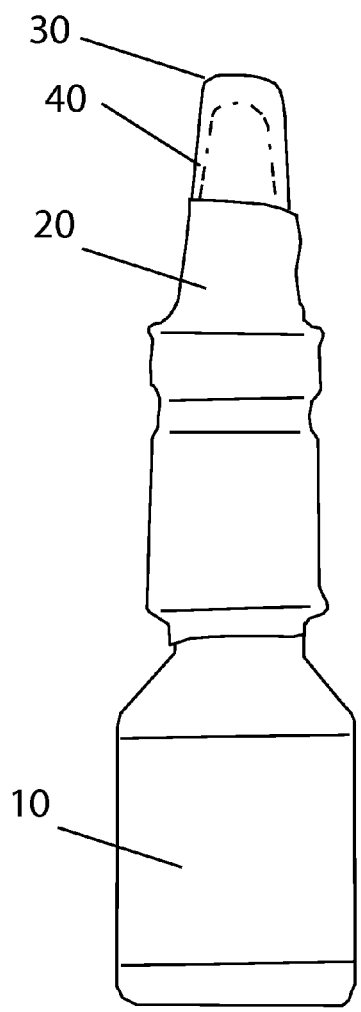
FIGS. 1A-1D illustrate side views of a nasal spray applicator at various stages between a shipping configuration and a usage configuration.

FIGS. 1A-1D illustrate side views of nasal spray applicator at various stages between a shipping configuration and a usage configuration. FIG. 1A shows a spray applicator in a shipping configuration where it may be attached to a container 10 such as a vial or bottle for holding a liquid medication. A shrink wrap sleeve 20 may be provided that may securely envelope the upper part of bottle 10 including its neck. The shrink wrap sleeve 20 may also envelope much of the spray applicator including a cap 30 that covers the nozzle 40.

Figure 1B:
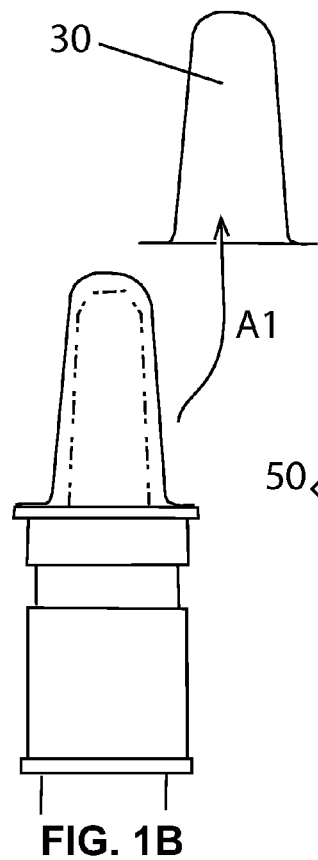
Figure 1C:
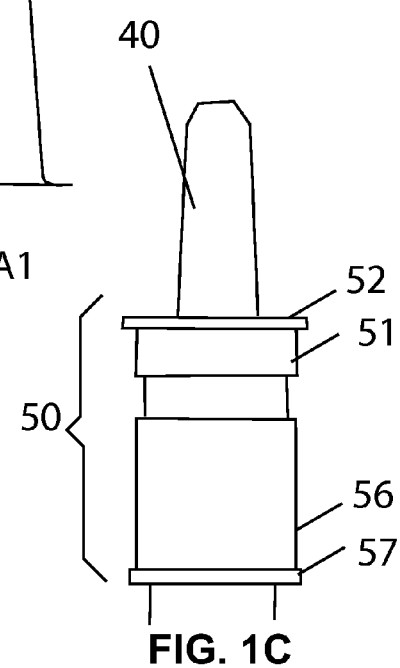

Once the shrink wrap sleeve 20 has been removed, FIG. 1B shows the cap 30 being removed from the assembly according to arrow A1. FIG. 1C shows the structure of the spray applicator, which may include nozzle 40. The nozzle may be supported on applicator body 50. The applicator body 50 may include several parts, such as upper portion 51 which may have an upper ledge 52, and lower portion 56 which may have a lower flange 57.

Figure 1D:
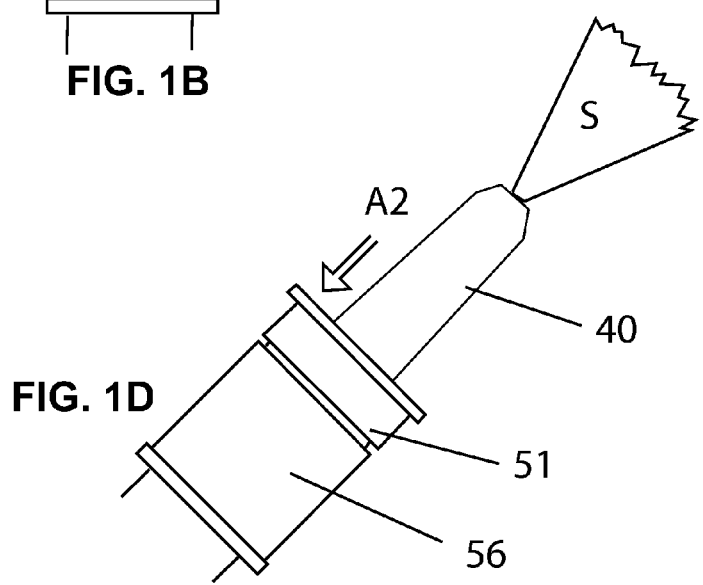

When the shrink wrap sleeve 20 has been removed and the cap 30 has been taken from the nozzle, the spray applicator may be actuated as shown in FIG. 1D by pressing or squeezing together (according to arrow A2) of the upper portion 51 and lower portion 56 of the spray applicator. This causes a spray S to be dispensed from nozzle 40.

The device shown in FIG. 1 has several disadvantages. Once the shrink wrap sleeve 20 is removed, the cap 30 is loose and may be misplaced. Also there is no longer a child resistant safety feature. Various embodiments of the invention shown in FIGS. 2-5 may overcome these disadvantages.

Figures 2A, 2B:
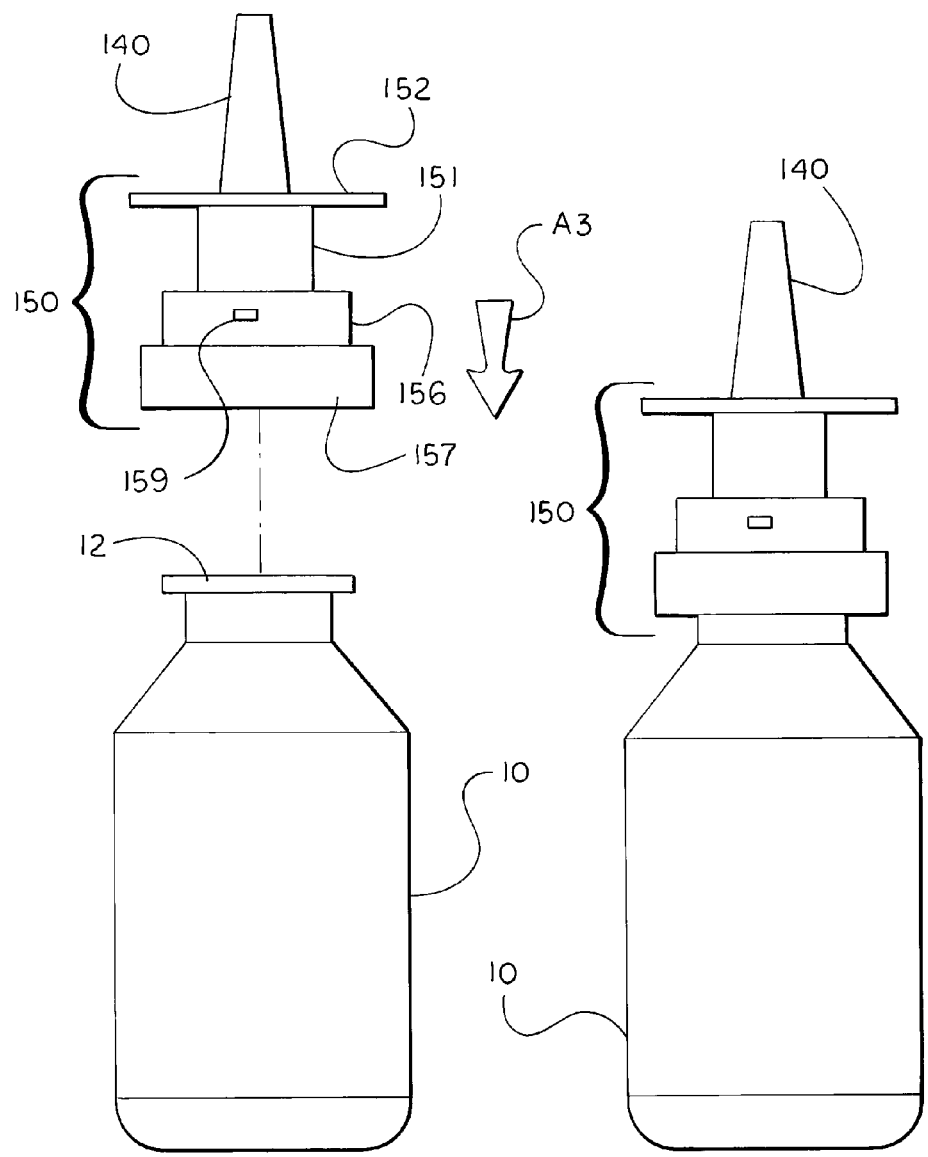
FIGS. 2A-2B illustrate side views of a nasal spray applicator being assembled, according to an embodiment of the invention.

FIG. 2A shows a bottle 10 with an upper lip 12 onto which a spray applicator 150 may be attached, for example by a snap-on fit of the applicator lower portion 156 onto the bottle lip 12 as indicated by arrow A3. Other methods of attachment may also be used, such as crimp-on, thread-on (advantageously with known anti-reversing features to prevent removing the applicator), adhesive attachment, and the like. Similarly to the applicator shown in FIG. 1, applicator 150 may include an upper portion 151. Upper portion 151 may include an upper ledge 152. A side engagement feature 159 may be provided on one or both sides of the applicator, for example on one or both sides of the lower portion 156. The engagement feature 159 may, by way of example, be a protrusion extending radially outward. FIG. 2B shows the applicator 150 having been attached to bottle 10.

FIGS. 3A-3B illustrate a safety device 200 according to various embodiments of the invention attached to applicator 150, after which the assembly may be attached to bottle 10 as denoted by arrow A4. It may be noted that although nozzle 140 is partially visible in the assembly, the nozzle outlet may be covered by safety device 200, thus serving in place of a cap 30. Also the safety device 200 when in place as shown in FIG. 3B may prevent actuation of the spray applicator 150.

It should be understood that the various parts of a safety device 200 may be single-piece or unitary parts, or the parts may be made of multiple subparts. For example, in some embodiments of the invention, side portions 240 may be formed as a single piece with other portions, or may be made of several separate pieces that are assembled or joined together in any suitable manner. The same is true of the other parts used in the safety device. In some embodiments, certain parts (such as side portions 240) could be bi-injected parts that include different materials.

FIG. 4 illustrates a side detail view of the safety device 200 in a closed configuration. The safety device may be made of a material such as plastic. Safety device 200 is shown with a base portion 210, for example a ring or loop that may fit around the neck of bottle 10. A hinge 220 such as a living hinge may connect the base portion 210 with an axial portion 230. The living hinge may be a bi-stable hinge such that it tends to remain in whichever position it is placed—either the closed position of FIG. 4 or the open position of FIG. 6.

Extending sideways from axial portion 230 may be provided two side portions 240 (which also might be considered lateral or wing portions) and a terminal portion 260 (which also might be considered an end, top, or upper portion). Side portions 240 may include engagement features 242 and/or release features 244. For example (as better shown on FIG. 6) the engagement feature 242 may be an aperture to receive a protrusion 159 in the side of the applicator 150. Alternately the engagement feature 242 may be an inward protrusion to engage an opening or depression 159 in the spray applicator. The release feature 244 may be an outwardly extending protrusion, which when pushed inwardly (for example by the user's thumb or finger) may cause the engagement feature 242 to rock outwardly and release from engagement feature 159. This rocking action may be realized for example by defining two U-shaped slots 245 around the engagement feature 242 and release feature 244, with a pivot portion 246 between the U-shaped slots 245.

The height Y2 of the side portion 240 may be sufficient to substantially fill the height Y1 between the lower surface of ledge 152 and the upper surface 157. This may inhibit squeezing or pressing on the nozzle to actuate the sprayer.

The top wall 260 may include a tamper evident feature 262 such as a break-away bar or retainer that must be removed before the spray actuator can be used. Behind or inward of the tamper evident feature 262 may be a tooth 264 (or other feature suitably shaped and sized) to cover the end of nozzle 140, even after the tamper evident features 262 is removed. The tooth 264 may have an angled or ramped surface to help it snap off or onto the end of nozzle 140. A release feature 266 such as a rocker button similar to those described for the side walls may be utilized to disengage tooth 264 from the end of the nozzle.

Attached to one or both of axial wall 230 and top wall 260 may be one or more eave walls 250 which may help enclose nozzle 140 in the closed configuration.

FIG. 5A illustrates a side detail view of the safety device 200 being grasped by a user's hand. The user's thumb T and an opposing finger F may press on release features 244 in order to release the safety device from the sprayer. The user's index finger I may at the same time pull back on the top of the safety device to help tilt it away from the sprayer.

FIG. 5B is a cross-section view (as seen from above) showing how the safety device is held in place, and FIGS. 5C-5D are cross-section views showing how the release is accomplished.

FIG. 5B illustrates a cross section showing side portion 240 partially encircling applicator lower portion 156. The side engagement features 159, 242 are engaged, for example protrusions 159 on each side of applicator lower portion 156 may extend into holes 242 in side portion 240. The engagement features prevent the side portion 240 from being moved away from the applicator, that is, to the left as shown in FIG. 5B.

FIG. 5C illustrates a cross section showing how the user's thumb T and finger F may press upon buttons 244 cause the engagement features 242 (e.g. holes) to move away from protrusions 159. This movement may be achieved by providing each button 244 on the same hingedly movable piece of material as the associated engagement feature 242, and pivoting that piece of material upon a pivot or fulcrum point 246 (also shown in FIG. 6). The fulcrum point 246 may be an attachment or attachments to the side portion 240 (e.g., similar to the pivot pins on a seesaw). As buttons 244 are pressed inward, engagement features 242 thus move outward, coming clear from protrusions 159. Then, as shown in FIG. 5D, the user may pivot the safety device 200 away from the applicator (e.g. to the left as shown in FIG. 5D). The pivoting motion not only moves side walls 240 to the left, but it pivots walls 240 upward, so that the ends 240A of the side walls 240 rise upward and over the protrusions 159. The edges of engagement features 242, for example the holes used here as engagement features, may be beveled or otherwise shaped or formed to easily clear the protrusions 159, once the buttons 244 are pushed inward.

When finished using the applicator, the user may rotate the safety device back to the position shown in FIG. 5B. The protrusions 159 may be slanted or ramped as shown so that the ends 240A glide past the protrusions 159, and the material forming the forward perimeter of engagement feature 242 rides over the protrusions 159 as well, until openings 242 once again close down around protrusions 159 to secure the safety device until the next use.

FIG. 6 illustrates a side detail view of the safety device 200 in an open configuration, which may be achieved by rotating the safety device according to arrow A6. With the side walls 240 rotated outward and downward, the spray applicator may be actuated by squeezing or pressing together the upper and lower parts of the applicator. Before the rotation to the usage position can occur, the engagement features must be released. In this example tooth 264 must be released from the nozzle 140 (for example by pressing rocker button 266) and the side engagement features 159, 242 must be released (for example as described previously by pressing rocker buttons 244). The safety device 200 may be configured so that all the rocker buttons must be pressed inward at the same time; thus requiring three fingers to release the safety device 200. Even if a small child is able to reason out the operation of the device, the spacing of the rocker buttons may be such that the small child's fingers are not able to reach all three buttons simultaneously with enough force to move the safety device to the usage configuration of FIG. 6.

After using the spray applicator, the user may rotate safety device 200 back to the position shown in FIG. 4 and FIG. 5B, at which position the three-point safety engagement features may once again take hold. It is not necessary to press on the three points in order to return to the safety position. The side walls 240 may have beveled or curved portions 249 to help clear the upper ledge 152 when moving between safety and operating configurations.

The safety device may thus provide a secure shipping configuration that prevents actuation during shipping. A tamper evident feature may be provided. A three-point release mechanism may need to be operated to bring the device to a usage position. The safety device may be adapted for repeated movement back and forth between the safety and the usage positions. The end portion may provide a cover for the applicator which remains attached to the assembly so that it will not be lost.

Having thus described certain particular embodiments of the invention, it is understood that the invention defined by the appended claims is not to be limited by particular details set forth in the above description, as many apparent variations thereof are contemplated. Rather, the invention is limited only be the appended claims, which include within their scope all equivalent devices or methods which operate according to the principles of the invention as described.

What is claimed is:

1. A safety device to be applied to a dispenser of the type actuated by an axial compression of a dispenser nozzle, the safety device comprising:
   a base portion secured to the dispenser nozzle or to a container attached to the dispenser nozzle;
   an axial portion with a first end hingedly attached to the base portion;
   a terminal portion attached to the axial portion at a second end opposite from the first end, the terminal portion having a tooth for engaging an outlet end of the dispenser nozzle;
   a pair of side portions attached to the axial portion between the first and second ends, the side portions each having a side engagement feature for engaging a side of the dispenser nozzle;
   wherein the safety device has a safety position and a dispense position,
   wherein the tooth and the two side engagement features each must be disengaged before the safety device can be moved from the safety position to the dispense position.

2. The safety device of claim 1, wherein the terminal portion comprises a first release mechanism to disengage the tooth from the outlet end of the nozzle.

3. The safety device of claim 2, wherein the first release mechanism comprises a rocking action.

4. The safety device of claim 1, wherein the side portions each comprise a side release mechanism to disengage the engagement feature.

5. The safety device of claim 4, wherein the side release mechanism comprises a rocking action.

6. The safety device of claim 1, wherein in the safety configuration the side portions block the nozzle from being actuated.

7. The safety device of claim 1, further comprising a removable tamper evident feature on the terminal portion.

* * * * *